US006595210B2

(12) United States Patent
Ohki et al.

(10) Patent No.: US 6,595,210 B2
(45) Date of Patent: Jul. 22, 2003

(54) INHALATOR FOR ADMINISTERING POWDER COMPOSITION

(75) Inventors: Hisatomo Ohki, Gunma (JP); Yoshiyuki Yazawa, Gunma (JP); Shigemi Nakamura, Gunma (JP); Mitsuru Yokobori, Gunma (JP); Kazunori Ishizeki, Gunma (JP)

(73) Assignee: Unisia Jecs Corporation, Atsugi (JP)

( * ) Notice: Subject to any disclaimer, the term of this patent is extended or adjusted under 35 U.S.C. 154(b) by 5 days.

(21) Appl. No.: 09/908,915

(22) Filed: Jul. 20, 2001

(65) Prior Publication Data

US 2002/0062829 A1 May 30, 2002

(30) Foreign Application Priority Data

Nov. 27, 2000 (JP) ....................................... 2000-359822
Nov. 29, 2000 (JP) ....................................... 2000-363636

(51) Int. Cl.[7] ....................... A61M 13/00; A61M 15/00; A61M 16/10; A61M 16/00; B65D 7/14; B65D 83/06

(52) U.S. Cl. ............................ 128/203.15; 128/203.12; 128/203.21; 128/203.23; 604/58

(58) Field of Search ....................... 128/203.19, 203.21, 128/203.12, 203.23, 203.15, 200.14, 200.24, 203.25, 203.24, 205.21; 604/58

(56) References Cited

U.S. PATENT DOCUMENTS

| | | | | | |
|---|---|---|---|---|---|
| 4,175,556 | A | * | 11/1979 | Freezer .................. | 128/203.23 |
| 4,227,522 | A | * | 10/1980 | Carris ................... | 128/203.15 |
| 4,338,931 | A | * | 7/1982 | Cavazza ................ | 128/203.15 |
| 5,239,993 | A | * | 8/1993 | Evans ................... | 128/203.15 |
| 5,320,714 | A | * | 6/1994 | Brendel ................. | 128/203.15 |
| 5,619,985 | A | * | 4/1997 | Ohki et al. ............ | 128/203.21 |
| 5,647,349 | A | * | 7/1997 | Ohki et al. ............ | 128/203.15 |
| 5,715,811 | A | * | 2/1998 | Ohki et al. ............ | 128/203.21 |
| 5,752,505 | A | * | 5/1998 | Ohki et al. ............ | 128/203.15 |
| 5,988,163 | A | * | 11/1999 | Casper et al. .......... | 128/203.15 |
| 5,996,577 | A | | 12/1999 | Ohki et al. ............ | 128/203.15 |
| 6,055,980 | A | * | 5/2000 | Mecikalski et al. .... | 128/203.15 |
| 6,123,070 | A | * | 9/2000 | Bruna et al. ........... | 128/203.15 |
| 6,240,918 | B1 | * | 6/2001 | Ambrosio et al. ..... | 128/203.15 |
| 6,273,086 | B1 | * | 8/2001 | Ohki et al. ............ | 128/203.21 |
| 6,298,846 | B1 | * | 10/2001 | Ohki et al. ............ | 128/203.15 |
| 6,325,061 | B1 | * | 12/2001 | Dagsland ............... | 128/203.15 |
| 6,371,111 | B1 | * | 4/2002 | Ohki et al. ............ | 128/203.15 |
| 6,408,846 | B1 | * | 6/2002 | Ohki et al. ............ | 128/203.15 |
| 6,427,688 | B1 | * | 8/2002 | Ligotke et al. ........ | 128/203.15 |
| 2002/0033177 | A1 | * | 3/2002 | Ohki et al. ............ | 128/203.15 |

FOREIGN PATENT DOCUMENTS

| | | | | |
|---|---|---|---|---|
| EP | 333334 A2 * | 9/1989 | .......... A61M/15/00 |
| JP | 62-41668 | 2/1987 | |
| JP | 63-06024 | 2/1988 | |
| JP | 09-47509 | 2/1997 | |
| WO | 97/36574 | 10/1997 | |

* cited by examiner

*Primary Examiner*—Henry Bennett
*Assistant Examiner*—Kathryn Ferko
(74) *Attorney, Agent, or Firm*—Foley & Lardner

(57) ABSTRACT

An inhalator including an inhalator body including a powder receiving chamber for receiving a powder, an air-powder mixture reservoir for temporarily storing an air-powder mixture flowing from the powder receiving chamber, and a diluent air passage for introducing a diluent air into the air-powder mixture reservoir. The air-powder mixture is formed within the powder receiving chamber when an air is introduced into the powder receiving chamber. The air-powder mixture within the air-powder mixture reservoir is admixed with a diluent air introduced thereinto through the diluent air passage. The diluted air-powder mixture is discharged from an air-powder mixture outlet into a user's oral or nasal cavity. A powder composition for inhalators includes at least two kinds of fine particles different in particle diameter.

15 Claims, 4 Drawing Sheets

INHALATOR FOR ADMINISTERING POWDER COMPOSITION

BACKGROUND OF THE INVENTION

The present invention relates to an inhalator suitable for administering a powder or powder composition, and a powder composition containing powders different in particle diameter from each other and a process for administering the powder composition using inhalators.

Generally, a powder inhalator is used for inhaling a powder or powder composition such as a powdered medicine into a human body through the oral or nasal cavity. The inhalator includes an inhalator body having an air intake path for introducing an ambient air and a suction opening through which an air-powder mixture within the inhalator body is sucked into the oral or nasal cavity. A powder receiving chamber for receiving the powder is disposed within the inhalator body and communicated with the outside of the inhalator body via the air intake path. An air-powder mixture path extends from the powder receiving chamber to the suction opening. The air-powder mixture is formed when the air is introduced into the powder receiving chamber through the air intake path. The air-powder mixture is then transmitted from the powder receiving chamber to the suction opening via the air-powder mixture path.

There are several types of powders different in aerodynamic mean particle diameter as follows: a powder having the aerodynamic mean particle diameter of not less than 7 $\mu$m and depositing in an oral cavity or hypoglottis, a powder having the aerodynamic mean particle diameter of 5–7 $\mu$m and depositing in a throat, a powder having the aerodynamic mean particle diameter of 3–5 $\mu$m and depositing in a trachea, a powder having the aerodynamic mean particle diameter of 1–3 $\mu$m and depositing in bronchi, and a powder having the aerodynamic mean particle diameter of not more than 1 $\mu$m and depositing into alveoli, and the like. The powder having the aerodynamic mean particle diameter of not more than 3 $\mu$m is required to surely reach affected areas of the human body. Also, the powder such as an acrid powder is preferably dosed in several parts upon being inhaled.

In addition, there has been proposed powder tobacco for use with the inhalator. The powder tobacco can be substituted for a usual smoking tobacco because the powder tobacco provides a smoking feeling upon being inhaled. When the powder tobacco is used, one dose of the powder tobacco is dispensed in parts from the inhalator upon each inhalation.

The human bronchi and alveoli exist in deeper portions of the human body. Therefore, in order to ensure stable deposit of the powder having the particle diameter of not more than 3 $\mu$m in the bronchi and alveoli, it is preferable to dose the powder in parts, i.e., dispense a small amount of the powder each inhalation.

However, in the earlier technique, the whole amount of the powder received within the powder receiving chamber of the inhalator is dispensed from the inhalator by the inhalation substantially at one time. If a dose of the powder having the particle diameter of not more than 3 $\mu$m is inhaled through the inhalator upon inhalation, a large amount of the powder dosed will be deposited in the oral cavity or trachea before being deposited in the bronchi and alveoli.

Further, there is known a process for administering a particulate medicament having a specific mean particle diameter into a patient's lungs upon the patient breathing. International Publication No. WO97/36574 discloses a process and device for inhalation of particulate medicament. The process includes (i) providing an inhalator which contains at least one dose of medicament particles comprising spherical hollow particulates of respirable particle size suitable for deposition in a human lungs, and (ii) removing the spherical hollow particulates from the inhalator. In the earlier technique, the particulate medicament having the specific particle diameter is used with the inhalator, but there is not described inhalation on multi-purpose prescription, for instance, one-time inhalation of multiple particulate medicaments for the purpose of simultaneous deposition in different portions such as the trachea and the alveoli of the patient's body. In order to follow the multi-purpose prescription, it is required that the patient repeatedly inhales separate doses of particulate medicaments for different prescriptions, takes a specific particulate medicament formulated for the multi-purpose prescription, or is treated with the combination of various prescriptions including peroral medicament, injection, application of fomentation, and the like.

SUMMARY OF THE INVENTION

It is an object of the present invention to provide an inhalator capable of dispensing one dose of a powder or powder composition in parts therefrom.

It is another object of the present invention to provide a powder composition containing powders different in particle diameter from each other and a process for administering the powder composition using inhalators, which are suitable for simultaneous deposition in different portions of the human body by one-time inhalation.

According to one aspect of the present invention, there is provided an inhalator for administering an air-powder mixture, comprising:

- an inhalator body including an air intake path for introducing air into the inhalator body, and an air-powder mixture outlet for discharging the air-powder mixture from the inhalator body;
- a powder receiving chamber adapted to receive a powder, the powder receiving chamber being disposed within the inhalator body and communicated with an outside of the inhalator body through the air intake path;
- an air-powder mixture path adapted to transmit the air-powder mixture flowing from the powder receiving chamber to the air-powder mixture outlet;
- an air-powder mixture reservoir adapted to temporarily store the air-powder mixture flowing from the powder receiving chamber, the air-powder mixture reservoir being disposed within the air-powder mixture path; and
- a diluent air passage adapted to introduce a diluent air into the air-powder mixture reservoir, the diluent air passage communicating the air-powder mixture reservoir with the outside of the inhalator body.

According to a further aspect of the present invention, there is provided an inhalator for administering an air-powder mixture, comprising:

- a casing including an air intake inlet for introducing air into the casing, and an air-powder mixture outlet for discharging the air-powder mixture from the casing;
- powder receiving means for receiving a powder within the casing and permitting the powder to be admixed with the air introduced from the air intake inlet;
- air-powder mixture storing means for temporarily storing the air-powder mixture passing through the powder receiving means;

diluent air passage means for permitting a diluent air to flow into the air-powder mixture storing means; and air-powder mixture path means for permitting the air-powder mixture to flow from the powder receiving means to the air-powder mixture outlet via the air-powder mixture storing means.

According to another aspect of the present invention, there is provided a powder composition for use with an inhalator, comprising:

at least two kinds of fine particles selected from a first kind of fine particles having an aerodynamic mean particle diameter of not less than 7 μm, a second kind of fine particles having an aerodynamic mean particle diameter of 5–7 μm, a third kind of fine particles having an aerodynamic mean particle diameter of 3–5 μm, a fourth kind of fine particles having an aerodynamic mean particle diameter of 1–3 μm, and a fifth kind of fine particles having an aerodynamic mean particle diameter of not more than 1 μm.

According to a further aspect of the present invention, there is provided a process for administering a powder composition using an inhalator, comprising:

preparing the powder composition containing at least two kinds of fine particles selected from a first kind of fine particles having an aerodynamic mean particle diameter of not less than 7 μm, a second kind of fine particles having an aerodynamic mean particle diameter of 5–7 μm, a third kind of fine particles having an aerodynamic mean particle diameter of 3–5 μm, a fourth kind of fine particles having an aerodynamic mean particle diameter of 1–3 μm, and a fifth kind of fine particles having an aerodynamic mean particle diameter of not more than 1 μm;

supplying the powder composition to the inhalator; and discharging the powder composition from the inhalator.

The other objects and features of this invention will become understood from the following description with reference to the accompanying drawings.

DETAILED DESCRIPTION OF THE INVENTION

Referring to FIGS. 1–6, an inhalator, according to the present invention, of a preferred embodiment is explained.

Figure 1:
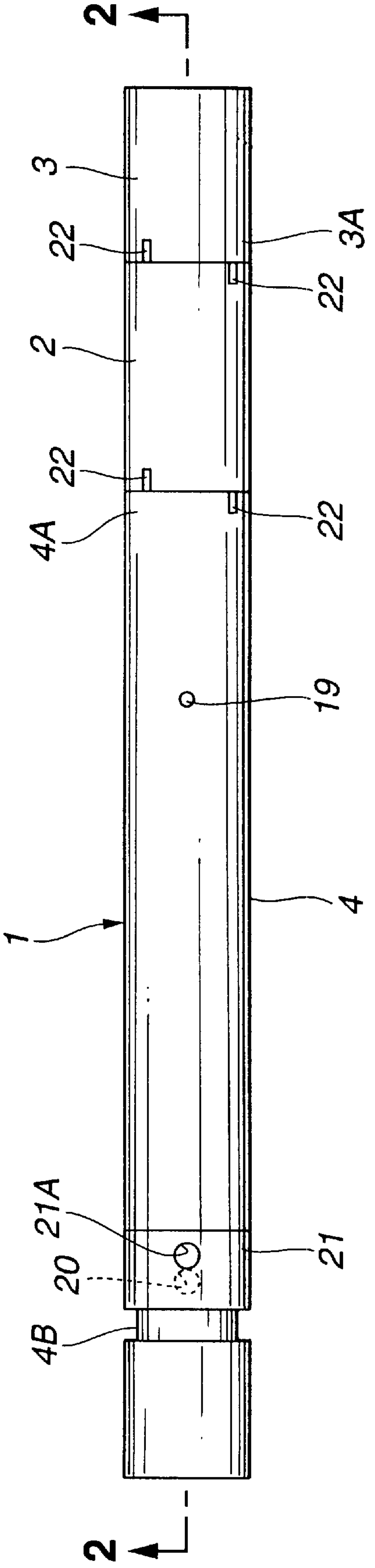
FIG. 1 is an elevation of an inhalator of a preferred embodiment, according to the present invention.

As illustrated in FIG. 1, the inhalator includes an inhalator body 1 as a casing which is formed into a cylindrical shape. Inhalator body 1 is made of a suitable resin material such as polypropylene, polystyrene, ABS resin and the like. Inhalator body 1 is constituted of cap 3, suction body 4 and capsule body 2 interposed between cap 3 and suction body 4. Cap 3 has air intake inlet 7A shown in FIG. 2, through which an ambient air is introduced into cap 3 and flows toward capsule body 2 and suction body 4 as explained later. Cap 3 has a length shorter than that of capsule body 2 and is rotatably connected with an upstream side of capsule body 2. Suction body 4 has air-powder mixture outlet 18 shown in FIG. 2, from which an air-powder mixture formed in inhalator body 1 is discharged into a user's oral cavity. Suction body 4 has a length longer than that of capsule body 2 and is rotatably connected with a downstream side of capsule body 2.

Figure 2:
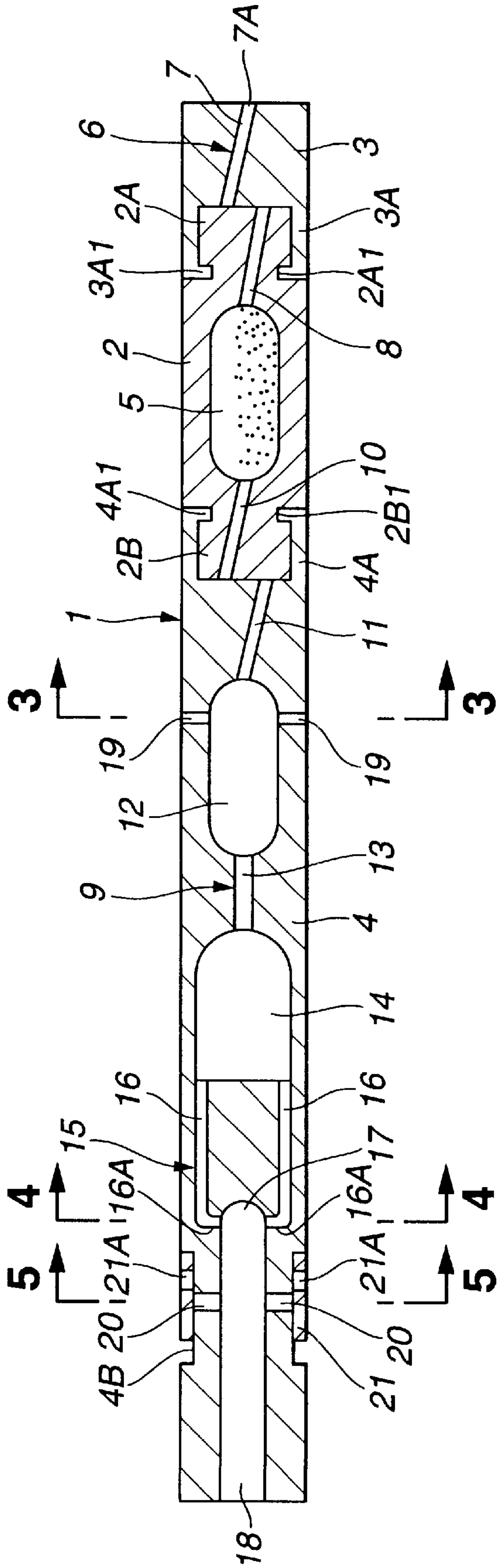
FIG. 2 is a longitudinal section of the inhalator, taken along the line 2—2 of FIG. 1, showing a rest position of the inhalator.

As illustrated in FIG. 2, capsule body 2 has engaging projection 2A and engaging groove 2A1 on the upstream end portion. Engaging projection 2A and engaging groove 2A1 axially adjacent thereto are engaged with engaging tube portion 3A and engaging projection 3A1 of cap 3, respectively. Capsule body 2 is coupled with cap 3 by the engagement of engaging projection 2A and engaging groove 2A1 with engaging tube portion 3A and engaging projection 3A1, respectively. Capsule body 2 also has at the downstream end portion, engaging projection 2B and engaging groove 2B1 axially adjacent thereto. Engaging projection 2B and engaging groove 2B1 are engaged with engaging tube portion 4A and engaging projection 4A1 of suction body 4, respectively. Capsule body 2 is coupled with suction body 4 by the engagement of engaging projection 2B and engaging groove 2B1 with engaging tube portion 4A and engaging projection 4A1, respectively.

Cocoon-shaped powder receiving chamber 5 is substantially coaxially disposed within capsule body 2. Powder receiving chamber 5 is provided for receiving a dose of a powder or powder composition such as particulate medicament, powder tobacco or the like. Powder receiving chamber 5 is in communication with the outside of inhalator body 1 through air intake path 6, when the inhalator is in a use position as explained later by referring to FIG. 6. The air-powder mixture is formed within powder receiving chamber 5 when the air flows into powder receiving chamber 5 via air intake path 6 in the use position of the inhalator.

Air intake path 6 is provided for introducing the air into powder receiving chamber 5. Air intake path 6 includes upstream intake passage 7 formed in cap 3 and downstream intake passage 8 formed in capsule body 2. Upstream intake passage 7 has an upstream end opening as air intake inlet 7A which is open to a generally central portion of an axial end face of cap 3. Upstream intake passage 7 has a downstream end opening that is open to a bottom of engaging tube portion 3A which mates with an axial end face of engaging projection 2A, in an offset position relative to the center axis of cap 3. Downstream intake passage 8 has an upstream end opening that is open to the axial end face of engaging projection 2A in an offset position relative to the center axis of capsule body 2. Downstream intake passage 8 has a downstream end opening that is open to an upstream end portion of powder receiving chamber 5 and in substantially alignment with the center axis of capsule body 2.

Figure 6:
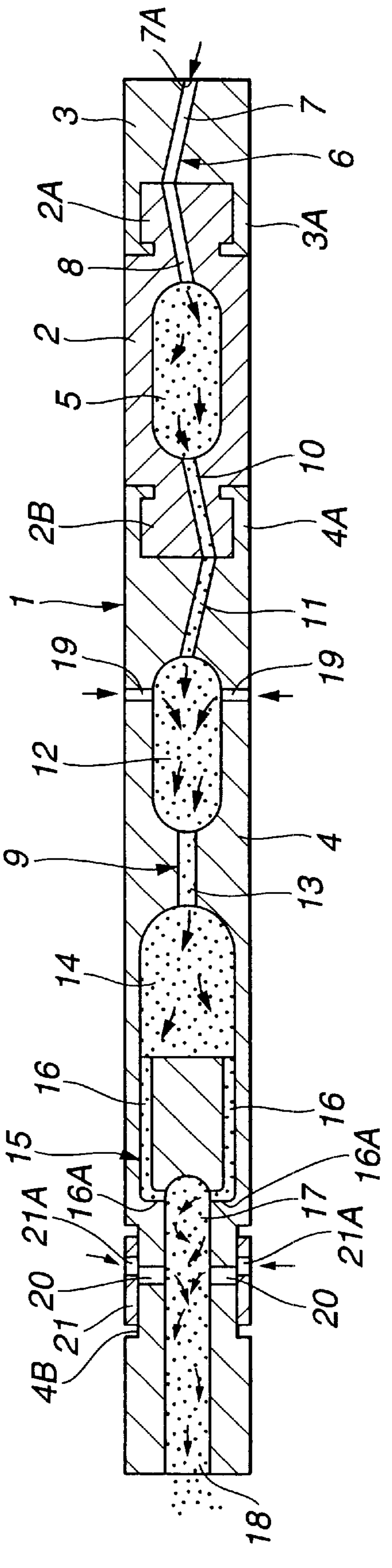
FIG. 6 is a view similar to FIG. 2, but showing a use position of the inhalator.

Capsule body 2 and cap 3 are relatively rotatable to be placed in a non-communication position shown in FIG. 2 and a communication position shown in FIG. 6. In the non-communication position, the downstream end opening of upstream intake passage 7 and the upstream end opening of downstream intake passage 8 are out of alignment with each other. Fluid communication between upstream intake passage 7 and downstream intake passage 8 is blocked so that powder receiving chamber 5 is prevented from being fluidly communicated with the outside of the inhalator. On the other hand, in the communication position, the downstream end opening of upstream intake passage 7 and the upstream end opening of downstream intake passage 8 are in fluid communication with each other. The fluid communication between upstream intake passage 7 and downstream intake passage 8 is established so that powder receiving chamber 5 is fluidly communicated with the outside of the inhalator. The opening area at the connection of upstream intake passage 7 and downstream intake passage 8 may be desirably regulated by adjusting the alignment of intake passages 7 and 8 to thereby control a flow amount of the air introduced into powder receiving chamber 5 and therefore control an amount of the powder in the air-powder mixture flowing from powder receiving chamber 5 toward air-powder mixture outlet 18.

Air-powder mixture path 9 extends between powder receiving chamber 5 and air-powder mixture outlet 18. Air-powder mixture path 9 permits the air-powder mixture to flow from powder receiving chamber 5 to air-powder mixture outlet 18 when the inhalator is in the use position.

First air-powder mixture reservoir 12 is disposed within air-powder mixture path 9. Air-powder mixture reservoir 12 is disposed in substantially coaxial with suction body 4. Air-powder mixture reservoir 12 is adapted to be communicated with powder receiving chamber 5 through discharge passage 10 and connecting passage 11 of air-powder mixture path 9. Air-powder mixture reservoir 12 has a cocoon shape having a volumetric capacity greater than a volumetric capacity of connecting passage 11. Air-powder mixture reservoir 12 having the greater volumetric capacity allows the air-powder mixture flowing thereinto through connecting passage 11 to be temporarily stored.

Discharge passage 10 is formed in capsule body 2 so as to be open to powder receiving chamber 5 at the upstream end and to engaging projection 2B at the downstream end. An upstream end opening of discharge passage 10 is open to a downstream end portion of powder receiving chamber 5 and in substantially alignment with the center axis of capsule body 2. A downstream end opening of discharge passage 10 is open to an axial end face of engaging projection 2B in an offset position relative to the center axis of capsule body 2. Connecting passage 11 is formed in suction body 4 so as to be open to engaging tube portion 4A at the upstream end and to air-powder mixture reservoir 12 at the downstream end. An upstream end opening of connecting passage 11 is open to a bottom of engaging tube portion 4A which mates with the axial end face of engaging projection 2B, in an offset position relative to the center axis of suction body 4. A downstream end opening of connecting passage 11 is open to an upstream end portion of air-powder mixture reservoir 12 and in substantially alignment with the center axis of suction body 4. Capsule body 2 and suction body 4 are relatively rotatable so as to be placed in a non-communication position shown in FIG. 2 and a communication position shown in FIG. 6. In the non-communication position, the downstream end opening of discharge passage 10 and the upstream end opening of connecting passage 11 are out of alignment with each other so that fluid communication between discharge passage 10 and connecting passage 11 is blocked. Powder receiving chamber 5 is prevented from being fluidly communicated with air-powder mixture reservoir 12. On the contrary, in the communication position, the downstream end opening of discharge passage 10 and the upstream end opening of connecting passage 11 are in fluid communication with each other. The fluid communication between discharge passage 10 and connecting passage 11 is established so that powder receiving chamber 5 is fluidly communicated with the air-powder mixture reservoir 12. The opening area at the connection of discharge passage 10 and connecting passage 11 may be desirably regulated by adjusting the alignment of discharge passage 10 and connecting passage 11 to thereby control an amount of the air-powder mixture flowing from powder receiving chamber 5 into air-powder mixture reservoir 12.

Figure 3:
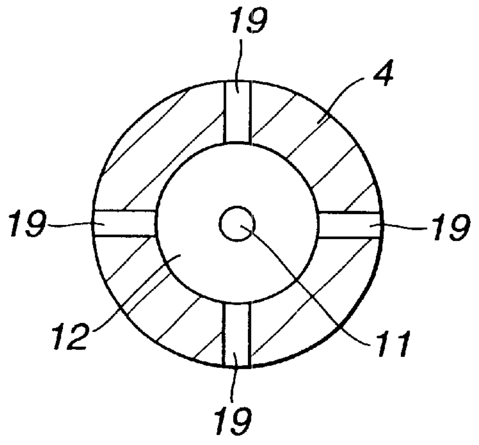
FIG. 3 is an enlarged section of the inhalator, taken along the line 3—3 of FIG. 2.

First diluent air passage 19 is formed in suction body 4 and communicated with air-powder mixture reservoir 12. Diluent air passage 19 introduces a diluent air into air-powder mixture reservoir 12 when the air-powder mixture flows from powder receiving chamber 5 into air-powder mixture reservoir 12. The diluent air introduced is merged in the air-powder mixture within air-powder mixture reservoir 12 to thereby dilute the air-powder mixture. The diluted air-powder mixture flowing from air-powder mixture reservoir 12 has a reduced flow rate and a decreased mixing ratio of the powder relative to the air which are present in the diluted air-powder mixture. Diluent air passage 19 is constituted of four passages arranged in crossed manner in lateral section in this embodiment as shown in FIG. 3. As illustrated in FIG. 3, each of four diluent air passages 19 has an inlet open to an outer circumferential surface of suction body 4 and an outlet open to a circumferential surface of air-powder mixture reservoir 12.

Second air-powder mixture reservoir 14 is disposed within air-powder mixture path 9 downstream of first air-powder mixture reservoir 12. Air-powder mixture reservoir 14 is disposed in substantially coaxial relation to suction body 4. Air-powder mixture reservoir 14 is communicated with air-powder mixture reservoir 12 through communication passage 13 of connecting passage 11 which extends in the axial direction of suction body 4. Air-powder mixture reservoir 14 has a bell shape having a volumetric capacity greater than a volumetric capacity of communication passage 13 when viewed in axial cross-section. Air-powder mixture reservoir 14 with the greater volumetric capacity allows the air-powder mixture flowing thereinto through communication passage 13 to be temporarily stored.

Figure 4:
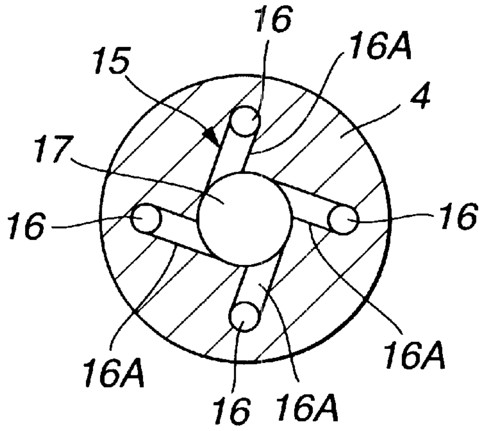
FIG. 4 is an enlarged section of the inhalator, taken along the line 4—4 of FIG. 2.
Figure 5:
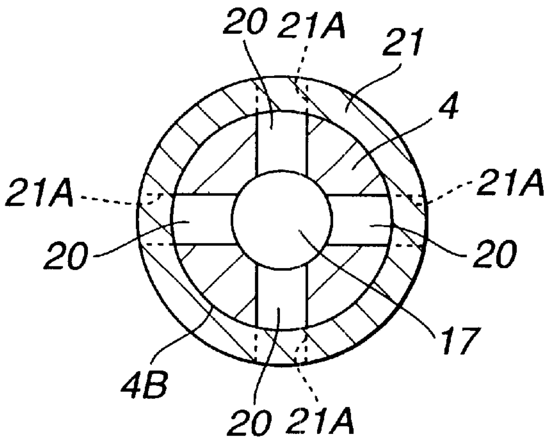
FIG. 5 is an enlarged section of the inhalator, taken along the line 5—5 of FIG. 2.

Dispersion part 15 is disposed within air-powder mixture path 9 downstream of second air-powder mixture reservoir 14. Dispersion part 15 is adapted to prevent the powder in the air-powder mixture flowing from second air-powder mixture reservoir 14 from aggregating together and intimately mix the powder and the air to form a uniform air-powder mixture. Dispersion part 15 includes dispersion chamber 17 and a plurality of dispersion passages 16 connected with dispersion chamber 17. Dispersion passages 16, four passages in this embodiment, connect dispersion chamber 17 with air-powder mixture reservoir 14. Each of dispersion passages 16 has an inlet open to air-powder mixture reservoir 14 and an outlet open to dispersion chamber 17. Specifically, dispersion passage 16 includes an inlet passage portion extending from an outer peripheral portion of air-powder mixture reservoir 14 in the axial direction of suction body 4. Dispersion passage 16 also includes outlet passage portion 16A that radially inwardly extends from a downstream side of the inlet passage portion and is open to an upstream end portion of dispersion chamber 17. As illustrated in FIG. 4, dispersion chamber 17 has a generally circular-shaped section and outlet passage portion 16A extends in a tangential direction of dispersion chamber 17. The air-powder mixture flowing into dispersion chamber 17 through dispersion passages 16 forms a swirl flow within dispersion chamber 17. The swirl flow of the air-powder mixture prevents the powder in the air-powder mixture from forming an aggregated mass of the powder.

Second diluent air passage 20 is formed within suction body 4 in communication with dispersion chamber 17. As seen from FIGS. 2 and 5, four diluent air passages 20 radially extend from grooved portion 4B on an outer surface of suction body 4 to dispersion chamber 17. Grooved portion 4B extends along the entire circumference of the outer surface of suction body 4. Diluent air passages 20 introduce the ambient air as a diluent air into dispersion chamber 17 when the air-powder mixture within dispersion chamber 17 is directed toward outlet 18 by the user's suction.

Regulator 21 for variably controlling a flow amount of the diluent air introduced into dispersion chamber 17 via diluent air passages 20 is axially moveably disposed on grooved portion 4B of suction body 4. Regulator 21 is in the form of a ring in this embodiment. Regulator 21 has four regulator holes 21A coming into alignment with diluent air passages 20 by the axial movement of the regulator 21. Regulator 21 variably regulates an opening area of each of diluent air passages 20 to thereby variably control the flow amount of the diluent air which is merged in the air-powder mixture within dispersion chamber 17.

The air-powder mixture passing through dispersion passages 16 and dispersion chamber 17 flows to air-powder mixture outlet 18 from which the air-powder mixture is dispensed into the user's oral cavity. Air-powder mixture outlet 18 is communicated with dispersion chamber 17 and open to one axial end surface of suction body 4. Air-powder mixture outlet 18 is disposed substantially coaxially with the center axis of suction body 4.

Referring back to FIG. 1, counter or registration marks 22, 22, 22 are formed on the upstream and downstream end portions of the outer circumferential surface of capsule body 2, downstream engaging tube portion 3A of cap 3, and upstream engaging tube portion 4A of suction body 4, respectively. When counter mark 22 on the upstream-end side of capsule body 2 is aligned with counter mark 22 on the downstream-end side of cap 3, upstream and downstream intake passages 7 and 8 of air intake path 6 are communicated with each other. When counter mark 22 on the downstream-end side of capsule body 2 is aligned with counter mark 22 on the upstream-end side of suction body 4, discharge passage 10 and connecting passage 11 of air-powder mixture path 9 are communicated with each other.

An operation of the thus-constructed inhalator of the present invention will be explained hereinafter.

When the inhalator is in a rest or nonuse position shown in FIG. 2, upstream and downstream intake passages 7 and 8 of air intake path 6 are fluidly disconnected from each other and discharge passage 10 and connecting passage 11 of air-powder mixture path 9 are fluidly disconnected from each other. In this state, powder receiving chamber 5 is prevented from being fluidly communicated with the outside of inhalator body 1 and air-powder mixture reservoir 12. Thus, if the inhalator is in the rest position, the powder received within powder receiving chamber 5 can be restrained from flowing therefrom and inhalator body 1 when the user carries the inhalator.

Next, upon using the inhalator, cap 3 and suction body 4 are rotated relative to capsule body 2 to align respective counter marks 22 with each other. Regulator 21 is axially moved in grooved portion 4B so as to desirably adjust the opening area of second diluent air passage 20. The inhalator is thus placed in a use position shown in FIG. 6. In the use position, upstream and downstream intake passages 7 and 8 of air intake path 6 are fluidly connected with each other and discharge passage 10 and connecting passage 11 of air-powder mixture path 9 are fluidly connected with each other. Powder receiving chamber 5 is allowed to be in fluid communication with the outside of inhalator body 1 and air-powder mixture reservoir 12. In this state, air-powder mixture outlet 18 of inhalator body 1 is put into the user's oral cavity and the ambient air is sucked by the user. The air is introduced into air intake path 6 through air intake inlet 7A. The air then flows into powder receiving chamber 5 as indicated by arrows in FIG. 6. The introduced air is admixed with the dose of the powder within powder receiving chamber 5, forming the air-powder mixture. The air-powder mixture flows into first air-powder mixture reservoir 12 via discharge passage 10 and connecting passage 11 of air-powder mixture path 9. The air-powder mixture is temporarily stored within air-powder mixture reservoir 12 and admixed with the diluent air introduced through diluent air passage 19. The thus diluted air-powder mixture has a decreased flow rate flowing into communication passage 13, and a reduced mixing ratio of the powder in the diluted air-powder mixture to the air in the diluted air-powder mixture.

The diluted air-powder mixture within first air-powder mixture reservoir 12 flows into second air-powder mixture reservoir 14 via communication passage 13 and then enters into dispersion chamber 17 via dispersion passages 16. There occurs a swirl flow of the diluted air-powder mixture within dispersion chamber 17. The swirl flow atomizes an aggregated mass of the powder which remains in dispersion chamber 17, to thereby assure the air-powder mixture containing fine particles of the powder in a suitably dispersed state. The air-powder mixture within dispersion chamber 17 is diluted by the diluent air introduced thereinto through second diluent air passage 20 and regulator holes 21A of regulator 21. The thus diluted air-powder mixture then is discharged from air-powder mixture outlet 18 into the user's oral cavity.

As be appreciated from the above explanation, the air-powder mixture flowing from powder receiving chamber 5 is diluted within air-powder mixture reservoir 12 by the diluent air introduced into air-powder mixture reservoir 12 through diluent air passage 19. A flow rate of the air-powder mixture is reduced within air-powder mixture reservoir 12 by the introduction of the diluent air. As a result, a part of the dose of the powder received within powder receiving chamber 5 is sucked by one-time inhalation by the user. Therefore, the dose of the powder received within powder receiving chamber 5 can be divided into a plurality of dose parts each being sucked by the user. Thus, the user can suck a small amount of the powder that forms each dose part, by one-time inhalation. If it is required to deposit fine particulate medicament having a small particle diameter in the bronchi or alveoli of a patient, a dose of the medicament can be dispensed in parts which are inhaled by multiple-time inhalation of the user through the inhalator of the invention. The fine particulate medicament can be prevented from being deposited in the trachea and be stably deposited in the bronchi or alveoli by multiple-time inhalation of the dose parts. The inhalator of the invention can be effectively used for dispensing a dose of a powder or powder composition such as particulate medicament and powder tobacco, in parts by multiple-time inhalation.

Further, with the arrangement of second diluent air passage 20 and regulator 21 for regulating the opening area of diluent air passage 20, an amount of the diluent air introduced into dispersion chamber 17 can be desirably regulated by axially moving regulator 21. A mixing ratio between the powder and the air present in the air-powder mixture within dispersion chamber 17 can be readily controlled by the regulation of the diluent air to be introduced. Accordingly, an amount of the powder which is sucked by one-time inhalation by the user, can be desirably controlled using regulator 21 depending on the user's liking, kinds of particulate medicaments, or the like. This can improve a performance of the inhalator. The amount of the powder for one-time inhalation may be controlled by regulating the opening area at the connection of upstream and downstream intake passages 7 and 8 of air intake path 6 or the opening area at the connection of discharge passage 10 and connecting passage 11 of air-powder mixture path 9.

Furthermore, with the arrangement of dispersion passages 16 and dispersion chamber 17 at dispersion part 15, the swirl flow of the air-powder mixture can be produced within dispersion chamber 17, which atomizes an aggregated mass of the powder remaining in dispersion chamber 17 and forms the air-powder mixture containing the powder particles in a good dispersed state. This can improve a dispersion efficiency of the inhalator.

Further, upstream and downstream intake passages 7 and 8 of air intake path 6 is arranged to establish and block the fluid communication between powder receiving chamber 5 and the outside of inhalator body 1. When the inhalator is in the nonuse position, upstream and downstream intake passages 7 and 8 are disconnected from each other so that the fluid communication between powder receiving chamber 5 and the outside of inhalator body 1 is blocked. In addition, discharge passage 10 and connecting passage 11 of air-powder mixture path 9 is arranged to allow and block the fluid communication between powder receiving chamber 5 and first air-powder mixture reservoir 12. In the nonuse position of the inhalator, discharge passage 10 and connecting passage 11 are disconnected from each other so that the fluid communication between powder receiving chamber 5 and first air-powder mixture reservoir 12 is blocked. With this arrangement of intake passages 7 and 8 and discharge passage 10 and connecting passage 11, the powder received within powder receiving chamber 5 can be prevented from flowing therefrom toward both air intake inlet 7A and air-powder mixture reservoir 12 upon the user carrying the inhalator. This can improve reliability of the inhalator. Further, when intake passages 7 and 8 are communicated with each other upon using the inhalator, the opening area of the connection of intake passages 7 and 8 can be regulated to control the flow amount of the air flowing into powder receiving chamber 5. Therefore, the amount of the powder present in the air-powder mixture produced within powder receiving chamber 5 can be adjusted. Similarly, upon communication of discharge passage 10 and connecting passage 11, the opening area of the connection thereof can be regulated to control the flow amount of the air-powder mixture flowing from powder receiving chamber 5 into air-powder mixture reservoir 12. The amount of the powder in the air-powder mixture flowing from air-powder mixture reservoir 12 toward air-powder mixture outlet 18 can be adjusted, and therefore, the amount of the powder to be sucked can be adjusted.

Although two air-powder mixture reservoirs 12 and 14 are provided within suction body 4 in this embodiment, a single air-powder mixture reservoir or three or more air-powder mixture reservoirs may be provided.

In addition, a capsule chamber for storing a capsule having a dose of the powder may be substituted for powder receiving chamber 5. In this case, the capsule within the capsule chamber may be pierced using a piercing device upon inhalation.

Further, a shutter member may be provided for blocking and allowing the fluid communication between powder receiving chamber 5 and the outside of inhalator body 1 and air-powder mixture reservoir 12, instead of the arrangement of upstream and downstream intake passages 7 and 8 of air intake path 6 and discharge passage 10 and connecting passage 11 of air-powder mixture path 9. The shutter member may be rotatably or slidably disposed within air intake path 6 extending between powder receiving chamber 5 and air intake inlet 7A and the portion of air-powder mixture path 9 which extends between powder receiving chamber 5 and air-powder mixture reservoir 12.

Furthermore, either one of the upstream end portion of capsule body 2 and engaging tube portion 3A of cap 3 may have on the outer circumferential surface a groove circumferentially extending within a predetermined angular region. The other may have on the outer circumferential surface a projection engageable with the groove such that both capsule body 2 and cap 3 are rotatably moveable to each other in the predetermined angular region. A similar circumferentially extending groove may be formed on either one of the outer circumferential surface of the downstream end portion of capsule body 2 and the outer circumferential surface of engaging tube portion 4A of suction body 4, and a similar projection may be formed on the other thereof. If the projections reach the respective ends of the grooves, the communication between upstream and downstream intake passages 7 and 8 and the communication between discharge passage 10 and connecting passage 11 will be established. In this case, counter marks 22 can be omitted.

Next, a powder composition for use with inhalators and a process for administering the powder composition using inhalators, according to the present invention, will be explained hereinafter.

The powder composition is suitable to be administered from an oral or nasal cavity for deposition in inside parts of the human body. The powder composition includes at least two kinds of fine particles selected from a group consisting of a first kind of fine particle having an aerodynamic mean particle diameter of not less than 7 μm, a second kind of fine particle having an aerodynamic mean particle diameter of 5–7 μm, a third kind of fine particle having an aerodynamic mean particle diameter of 3–5 μm, a fourth kind of fine particle having an aerodynamic mean particle diameter of 1–3 μm, and a fifth kind of fine particle having an aerodynamic mean particle diameter of not more than 1 μm. The first kind of fine particle having the aerodynamic mean particle diameter of not less than 7 μm is deposited in an oral cavity or hypoglottis of a human body. The second kind of fine particle having the aerodynamic mean particle diameter of 5–7 μm is deposited in a throat of a human body. The third kind of fine particle having the aerodynamic mean particle diameter of 3–5 μm is deposited in a trachea of a human body. The fourth kind of fine particle having the aerodynamic mean particle diameter of 1–3 μm is deposited in bronchi of a human body. The fifth kind of fine particle having the aerodynamic mean particle diameter of not more than 1 μm is deposited in alveoli of a human body.

Preferably, the fine particles of the powder composition of the present invention have a significantly narrow particle size distribution. More preferably, the fine particles have the particle size distribution consistent with a predetermined range of an aerodynamic mean particle diameter which is required for deposition in the respective parts of the human body.

The powder composition may be powder tobacco and particulate medicament. The powder tobacco contains at least two kinds of fine particles selected from the first, third and fifth kinds of fine particles as described above. For instance, the powder tobacco may contain fine particles as a gustatory component which have the aerodynamic mean particle diameter of 45–55 μm for deposition in the oral cavity or hypoglottis, fine particles as a stimulatory component which have the aerodynamic mean particle diameter of 3–5 μm for deposition in the trachea or throat, and fine particles as an agent which have the aerodynamic mean particle diameter of 0.5–2 μm for deposition in the alveoli or bronchi. A coffee extract powder may be used for the fine particles as a gustatory component having the aerodynamic mean particle diameter of 45–55 μm. A menthol extract powder may be used for the fine particles as a stimulatory component having the aerodynamic mean particle diameter of 3–5 μm. A nicotine extract powder may be used for the fine particles as an agent having the aerodynamic mean particle diameter of 0.5–2 μm. If the powder tobacco is inhaled with the inhalator, the same taste, stimulus and nicotinic effect as those obtained by smoking can be obtained.

The particulate medicament as the powder composition of the present invention contains at least two kinds of fine particles selected from the first through fifth kinds of fine particles as described above. The particulate medicament may contain fine particles as a gustatory component which have the aerodynamic mean particle diameter of 60–80 μm for deposition in the oral cavity or hypoglottis, fine particles as an antiphlogistic agent which have the aerodynamic mean particle diameter of 4–6 μm for deposition in the trachea or throat, and fine particles as an agent which have the aerodynamic mean particle diameter of 1–3 μm for deposition in the alveoli or bronchi. A powdered troche or candy may be used for the fine particles as a gustatory component having the aerodynamic mean particle diameter of 60–80 μm. An antiphlogistic powder may be used for the fine particles as an antiphlogistic agent having the aerodynamic mean particle diameter of 4–6 μm. An antibiotic powder may be used for the fine particles as an agent having the aerodynamic mean particle diameter of 1–3 μm.

In addition, the particulate medicament as the powder composition of the present invention may be selected from an analgesic agent, an anginal preparation, an antiallergic agent, an anti-infective agent, an antihistaminic agent, an anti-inflammatory agent, an antitussive agent, a bronchodilator agent, a diuretic agent, an anticholinergic agent, and the like, depending on cure purposes. These powder agents may have various aerodynamic mean particle diameters suitable for deposition in different target parts of the human body.

If required, the particulate medicament as the powder composition of the present invention may be used together with a known excipient acceptable for inhalation into the human body. The composition of the particulate medicament is prepared in accordance with the doctor's prescription given on the basis of the patient's symptom.

In the administration process of the present invention, first the powder composition is prepared so as to contain at least two kinds of fine particles selected from the first to fifth kinds of fine particles as described above. The at least two kinds of fine particles of the powder composition may be blended together. The thus prepared powder composition is supplied to an inhalator suitable for dispensing a powder into the human body. The powder composition may be capsulated and then accommodated in the inhalator. Subsequently, the powder composition supplied is discharged from the inhalator. If the above-described inhalator of the present invention is used, the powder composition may be dispersed within the inhalator and then discharged therefrom without aggregation of the fine particles of the powder composition.

The powder composition and administration process of the present invention can be suitably used for cure of multiple diseases using the particulate medicaments which have effects on the multiple diseases, respectively. Specially, the powder composition and administration process of the present invention is suitable for providing analgesia and curing inflammation in the oral cavity and/or throat, asthma, bronchitis, COPD (chronic obstructive pulmonary disease), respiratory disease such as thoracho-infection, and allergosis.

The inhalators useable in this embodiment are described in Japanese Patent Applications First Publication Nos. 62-41668 and 9-47509, Japanese Patent Application Second Publication No. 63-6024, and U.S. Pat. No. 5,996,577.

EXAMPLES

The present invention is described in more detail by way of examples. However, these examples are only illustrative and not intended to limit a scope of the present invention thereto.

Example 1

A dose of a powder tobacco was prepared by blending 5 mg of coffee extract particulates having an aerodynamic mean particle diameter of 50 μm, 10 mg of menthol extract particulates having an aerodynamic mean particle diameter of 4 μm, and 1 mg of nicotine extract particulates having an aerodynamic mean particle diameter of 0.5–2 μm together. The thus prepared dose of a powder tobacco was supplied to a suitable inhalator as described above and then discharged from the inhalator.

Example 2

A dose of a particulate medicament mixture was prepared by blending candy particles having an aerodynamic mean particle diameter of 70 μm, antiphlogistic agent particles having an aerodynamic mean particle diameter of 5 μm, antibiotic agent particles having an aerodynamic mean particle diameter of 2 μm together in accordance with a doctor's prescription. The thus prepared dose of a particulate medicament mixture was filled in a capsule. The thus capsulated dose of a particulate medicament mixture was accommodated in a suitable inhalator as described above and then discharged from the inhalator.

Using the powder composition and the administration process of the present invention, a dose of the powder composition containing the at least two kinds of fine particulates different in mean particle diameter from each other can be selected depending on the target parts of the human body in which the powder composition is required to be deposited, and can be deposited in the target parts by one-time inhalation using the inhalator. Namely, multipurpose dosage of particulate medicaments, for instance, deposition of the particulate medicaments in both of the trachea and the alveoli or all of the throat, the bronchi and the alveoli, can be achieved during the one-time inhalation.

Further, using the powder composition and the administration process of the present invention, the patient can dispense with multiple times of inhalation for dosing a plurality of particulate medicaments required in different prescriptions. Also, any specific compound of particulate medicaments may not be required for multi-purpose prescription.

Furthermore, in a case where the capsulated powder composition of particulate medicaments having different mean particle diameters is used, the patient can dispense with adjusting the amount of the powder composition required for each inhalation and the mixing ratio of the different kinds of particulate medicaments.

The entire contents of basic Japanese Patent Applications Nos. 2000-363636 filed on Nov. 29, 2000, and 2000-359822 filed on Nov. 27, 2000, inclusive of the specification, claims and drawings, are herein incorporated by reference.

Although the invention has been described above by reference to certain embodiments of the invention, the invention is not limited to the embodiments described above. Modifications and variations of the embodiment described above will occur to those skilled in the art, in light of the above teachings. The scope of the invention is defined with reference to the following claims.

What is claimed is:

1. An inhalator for administering an air-powder mixture, comprising:

an inhalator body including an air intake path for introducing an air into the inhalator body, and an air-powder mixture outlet for discharging the air-powder mixture from the inhalator body;

a powder receiving chamber adapted to receive a powder, the powder receiving chamber being disposed within the inhalator body and communicated with an outside of the inhalator body through the air intake path;

an air-powder mixture path adapted to transmit the air-powder mixture flowing from the powder receiving chamber to the air-powder mixture outlet;

an air-powder mixture reservoir adapted to temporarily store the air-powder mixture flowing from the powder receiving chamber, the air-powder mixture reservoir being disposed within the air-powder mixture path;

a diluent air passage adapted to introduce a diluent air into the air-powder mixture reservoir, the diluent air passage communicating the air-powder mixture reservoir with the outside of the inhalator body; and a second diluent air passage adapted to introduce a diluent air into the air-powder mixture path downstream of the air-powder mixture reservoir upon the air-powder mixture flowing from the air-powder mixture reservoir, and a regulator variably controlling an opening area of the second diluent air passage.

2. An inhalator for administering an air-powder mixture, comprising:

an inhalator body including an air intake path for introducing an air into the inhalator body, and an air-powder mixture outlet for discharging the air-powder mixture from the inhalator body;

a powder receiving chamber adapted to receive a powder, the powder receiving chamber being disposed within the inhalator body and communicated with an outside of the inhalator body through the air intake path;

an air-powder mixture path adapted to transmit the air-powder mixture flowing from the powder receiving chamber to the air-powder mixture outlet;

an air-powder mixture reservoir adapted to temporarily store the air-powder mixture flowing from the powder receiving chamber, the air-powder mixture reservoir being disposed within the air-powder mixture path;

a diluent air passage adapted to introduce a diluent air into the air-powder mixture reservoir, the diluent air passage communicating the air-powder mixture reservoir with the outside of the inhalator body; and a dispersion part adapted to disperse the powder in the air-powder mixture passing through the air-powder mixture path downstream of the air-powder mixture reservoir, wherein the dispersion part comprises a plurality of dispersion passages branched from the air-powder mixture path downstream of the air-powder mixture reservoir, and a dispersion chamber disposed within the air-powder mixture path downstream of the dispersion passages, each of the dispersion passages having an outlet passage portion that is open into the dispersion chamber and arranged to form a swirl flow of the air-powder mixture.

3. The inhalator as claimed in claim 2, wherein the dispersion chamber has a generally circular-shaped section and the outlet passage portion of each of the dispersion passages extends in a tangential direction of the dispersion chamber.

4. An inhalator for administering an air-powder mixture, comprising:

an inhalator body including an air intake path for introducing an air into the inhalator body, and an air-powder mixture outlet for discharging the air-powder mixture from the inhalator body;

a powder receiving chamber adapted to receive a powder, the powder receiving chamber being disposed within the inhalator body and communicated with an outside of the inhalator body through the air intake path;

an air-powder mixture path adapted to transmit the air-powder mixture flowing from the powder receiving chamber to the air-powder mixture outlet;

an air-powder mixture reservoir adapted to temporarily store the air-powder mixture flowing from the powder receiving chamber, the air-powder mixture reservoir being disposed within the air-powder mixture path; and a diluent air passage adapted to introduce a diluent air into the air-powder mixture reservoir, the diluent air passage communicating the air-powder mixture reservoir with the outside of the inhalator body, wherein the air intake path is arranged to allow and block fluid communication between the powder receiving chamber and the outside of the inhalator body, and wherein the air intake path comprises at least two passages having an alignment position where the at least two passages are in alignment with each other and an offset position where the at least two passages are out of alignment with each other.

5. An inhalator for administering an air-powder mixture, comprising:

an inhalator body including an air intake path for introducing an air into the inhalator body, and an air-powder mixture outlet for discharging the air-powder mixture from the inhalator body;

a powder receiving chamber adapted to receive a powder, the powder receiving chamber being disposed within the inhalator body and communicated with an outside of the inhalator body through the air intake path;

an air-powder mixture path adapted to transmit the air-powder mixture flowing from the powder receiving chamber to the air-powder mixture outlet;

an air-powder mixture reservoir adapted to temporarily store the air-powder mixture flowing from the powder receiving chamber, the air-powder mixture reservoir being disposed within the air-powder mixture path; and a diluent air passage adapted to introduce a diluent air into the air-powder mixture reservoir, the diluent air passage communicating the air-powder mixture reservoir with the outside of the inhalator body, wherein the air-powder mixture path is arranged to allow and block fluid communication between the powder receiving chamber and the air-powder mixture reservoir, and wherein the air-powder mixture path comprises at least two passages disposed between the powder receiving chamber and the air-powder mixture reservoir, the plurality of passages having an alignment position where the at least two passages are aligned with each other and an offset position where the at least two passages are offset from each other.

6. The inhalator as claimed in claim 2, further comprising a second air-powder mixture adapted to temporarily store the air-powder mixture flowing from the first air-powder mixture reservoir toward the dispersion passages of the dispersion part.

7. The inhalator as claimed in claim 6, wherein each of the dispersion passages comprises an inlet open into the second air-powder mixture reservoir.

8. An inhalator for administering an air-powder mixture, comprising:

a casing including an air intake inlet for introducing an air into the casing, and an air-powder mixture outlet for discharging the air-powder mixture from the casing;

powder receiving means for receiving a powder within the casing and permitting the powder to be admixed with the air introduced from the air intake inlet;

air-powder mixture storing means for temporarily storing the air-powder mixture passing through the powder receiving means;

diluent air passage means for permitting a diluent air to flow into the air-powder mixture storing means;

air-powder mixture path means for permitting the air-powder mixture to flow from the powder receiving means to the air-powder mixture outlet via the air-powder mixture storing means; and a second diluent air passage means for permitting a diluent air to flow into the air-powder mixture path means downstream of the air-powder mixture storing means upon the air-powder mixture flowing from the air-powder mixture storing means.

9. The inhalator as claimed in claim 8, further comprising a regulator variable controlling an opening area of the second diluent air passage means.

10. The inhalator as claimed in claim 8, further comprising air intake path means for permitting the air to flow from the air intake inlet into the powder receiving means.

11. The inhalator as claimed in claim 8, wherein the air-powder mixture path means allows and blocks fluid communication between the powder receiving means and the air-powder mixture storing means.

12. An inhalator for administering an air-powder mixture, comprising:

a casing including an air intake inlet for introducing an air into the casing, and an air-powder mixture outlet for discharging the air-powder mixture from the casing;

powder receiving means for receiving a powder within the casing and permitting the powder to be admixed with the air introduced from the air intake inlet;

air-powder mixture storing means for temporarily storing the air-powder mixture passing through the powder receiving means;

diluent air passage means for permitting a diluent air to flow into the air-powder mixture storing means;

air-powder mixture path means for permitting the air-powder mixture to flow from the powder receiving means to the air-powder mixture outlet via the air-powder mixture storing means; and dispersion means for preventing the powder in the air-powder mixture from being aggregated together, wherein the dispersion means comprises passages means for forming a swirl flow of the air-powder mixture and chamber means for receiving the swirl flow of the air-powder mixture.

13. The inhalator as claimed in claim 12, wherein the chamber means has a generally circular-shaped section and the passage means extends in a tangential direction of the chamber means.

14. The inhalator as claimed in claim 12, further comprising air intake path means for permitting the air to flow from the air intake inlet into the powder receiving means.

15. The inhalator as claimed in claim 12, wherein the air-powder mixture path means allows and blocks fluid communication between the powder receiving means and the air-powder mixture storing means.

* * * * *